United States Patent [19]

Fina et al.

[11] Patent Number: 4,999,190

[45] Date of Patent: Mar. 12, 1991

[54] PREPARATION OF $I_5$- POLYIODIDE DISINFECTANT RESINS

[75] Inventors: Louis R. Fina; Jack L. Lambert; Ronald L. Bridges, all of Manhattan, Kans.

[73] Assignee: Kansas State University Research Foundation, Manhattan, Kans.

[21] Appl. No.: 365,556

[22] Filed: Jun. 13, 1989

[51] Int. Cl.$^5$ .............................................. A61L 2/16
[52] U.S. Cl. ..................................... 424/79; 424/670; 521/31
[58] Field of Search ..................... 424/79, 150; 521/31

[56] References Cited

U.S. PATENT DOCUMENTS

| | | | |
|---|---|---|---|
| 3,817,860 | 6/1974 | Lambert et al. | 424/79 |
| 3,923,665 | 12/1975 | Lambert et al. | 424/150 |
| 4,076,622 | 2/1978 | Costin | 424/79 |
| 4,187,183 | 2/1980 | Hatch | 424/79 |
| 4,190,529 | 2/1980 | Hatch | 210/668 |
| 4,238,477 | 12/1980 | Lambert et al. | 210/501 |
| 4,420,590 | 12/1983 | Gartner | 525/326.1 |

OTHER PUBLICATIONS

Fina et al., Proceedings, Second World Congress, International Water Resources Association, vol. II, pp. 53–59, New Delhi, 1975.

Hatch et al., (1980), Ind. Eng. Chem. Prod. Res. Dev., 19: 259–263.

Lambert et al., (1980), Ind. Eng. Chem. Prod. Res. Dev., 19: 256–258.

Fina et al., Appl. Environ. Microbiol. (1982), 44: 1370–1373.

Marchin et al., (1983), Appl. Environ. Microbiol., 46 965–969.

Primary Examiner—Peter F. Kulkosky
Attorney, Agent, or Firm—Tilton, Fallon, Lungmus & Chestnut

[57] ABSTRACT

A method is provided for strong base anion exchange resins containing high concentrations of pentaiodide ($I_5^-$). The resins are prepared from highly concentrated solutions of $I_5^-$ and $I_3^-$-ions. The exchanged ions, such as chloried ($Cl^-$), are washed out of the resin after completion of the exchange reaction with the polyiodide ion mixture. The resulting product is a stable resin of predetermined $I_5^-$ *content, which is highly effective as a disinfectant for water, acting against water-borne bacteria, virus, and Giardia.*

9 Claims, No Drawings

PREPARATION OF $I_5^-$ POLYIODIDE DISINFECTANT RESINS

FIELD OF INVENTION

The field of this invention is polyhalide anion exchange resins which provide halogen for disinfection of water. More particularly, the field of the invention is polyiodide quaternary ammonium anion exchange resin disinfectants.

BACKGROUND OF INVENTION

Triiodide ($I_3^-$) anion exchange resins for disinfecting water are described in Taylor, et al. Appl. Microbiol. (1970), 20:720-722, U.S. Pat. Nos. 3,817,860 and 3,923,675, and Fina and Lambert, "Proceedings, Second World Congress, International Water Resources Association", Vol. II pp. 53-59, New Delhi, 1975. The disinfectant resins were prepared by contacting an anion exchange resin in chloride or sulfate form with a sodium or potassium triiodide solution. Typical concentrations of the triiodide ion were around one molar, and the contacting was carried out at room temperatures. The cited patents also describe alternative procedures. In one procedure (U.S. Pat. No. 3,817,860, column 5, line 74, and column 6, line 5), the anion exchange resin, such as a quaternary ammonium resin, is first converted from the chloride or sulfate form to an iodide form by being contacted with a potassium iodide solution. The resin is then contacted with a triiodide solution or with elemental iodine (U.S. Pat. No. 3,923,665, column 3, lines 62-69).

Methods for preparing quaternary ammonium anion exchange resin triiodide disinfectants were reviewed by Hatch, et al., Ind. Eng. Chem. Prod. Res. Dev. (1980), 19:259-263. If quaternary ammonium anion exchange resins as supplied by the manufacturer contain unconverted tertiary amine groups, they can be remethylated by reaction with methyl iodide or dimethyl sulfate. However, most strong base anion exchange resins are supplied in substantially fully methylated form. A fully quaternarized resin, for example, can provide more stable triiodide disinfectants. In one of the methods described ("Method A"), enough aqueous triiodide ion to the resin was used to convert 97% of the anion sites. The triiodide solution was prepared with the stoichiometric amounts of potassium iodide and iodine, which were dissolved "in a near-minimum amount of water". The solution was stirred with the resin beads for 24 hours to complete the conversion. No heating is described so it can be assumed these procedures were all carried out at room temperature.

Pentaiodide quaternary ammonium resins and their properties were described by Lambert, et al in Ind. Eng. Chem. Prod. Res. Dev. (1980) 19:256-258. An $I_5^-$ resin was prepared from an $I_3^-$ resin by dissolving iodine in heated water and passing the water through the resin by a continuous recycle procedure. The $I_3^-$ resin used as a starting material was prepared by a previously disclosed procedure in which an aqueous solution of triiodide is applied to the resin. It was found that at the recommended recycle temperature of about 60° C., the $I_5^-$ resin could be produced in as little as 10 hours, but only on a small scale. This reference also described the preparation of an $I_7^-$ resin from the $I_5^-$ resin by a similar recycle procedure.

U.S. Pat. No. 4,238,477 discloses a procedure for preparing polyiodide quaternary ammonium anion exchange resins similar to that described in Lambert, et al. (1980), cited above. The patent states that the procedure can be used to prepare $I_3^-$, $I_5^-$, $I_7^-$ or mixed polyiodide resins. Mixed polyiodide resins are also described in U.S. Pat. Nos. 4,187,183 and 4,190,529, a mixed polyhalide resin is disclosed in U.S. Pat. No. 4,420,590.

The mixed polyiodide resins disclosed in (U.S. Pat. Nos. 4,187,183 and 4,190,529 contained both $I_3^-$ and $I_5^-$ groups. From 40 to 80% of the exchange sites were $I_3$ and from 1 to 30% were $I_5$ groups. The method of this preparation was similar to that described in Hatch, et al. (1980), cited above. Resin beads were placed in a container and covered with a minimum volume of water. A separate container of crystalline iodine and potassium or other water-soluble iodized salts was solubilized in just enough water to dissolve the reactants (col. 2, lines 35-36). After the reactants had completely dissolved, the solution was added to the water containing the resin, mixed therewith for sufficient time to complete adsorption of the polyiodide ions on the exchange sites of the resin, for example, from 24 to 72 hours. No molalities or molarities are specified with respect to the reaction solution and there is no disclosure of heating the reaction solution. Presumably, therefore, all steps of the method were carried out at room temperature.

Triiodide and pentaiodide resins function as broad spectrum bacteriacides against both Gram-positive and Gram-negative bacteria in water, and also against RNA and DNA viruses: Lambert, et al. (1980), cited above; and Fina, et al., Appl. Environ. Microbiol. (1982) 44:1370-1373. It has also been reported the pentaiodide or mixed polyiodide resins are effective as disinfectants against water-borne cysts of Giardia muris. and Giardia lamblia. Marchin, et al., Appl. Envron. Microbiol. (1983), 46:965-969.

Despite the great potential for $I_3^-$, $I_5^-$ and mixed polyiodide anion exchange resins for bacterial, viricidal, and Giardia disinfection of drinking water, these resins have thus far received only limited use. The available methods of producing polyiodide resins have not been adaptable to large scale economical production. The continuous cycle procedure using dilute solutions of iodine in warm water as described in U.S. Pat. No. 4,238,477 and Lambert, et al. (1980), cited above, have been limited to small scale production. The method is labor intensive and time consuming. For producing a mixed polyiodide resin a two-stage procedure is required in which the $I_3^-$ resin is first produced and then partially converted to include $I_5^-$ sites. Specially designed equipment is required for use in cycling a large volume of water at 50°-60° C. for as long as three to four days to produce the mixed resin. Even with careful preparation by this method, a resin of defined characteristics cannot be reliably produced For example, when a mixed resin containing $I_3^-$ and $I_5^-$ groups in preselected proportions is desired, the resulting product will contain a variable amount of $I_7^-$ groups.

SUMMARY OF INVENTION

This invention provides a direct method for preparing polyiodide strong base anion exchange resins containing high concentrations of $I_5^-$. The resins are prepared from highly concentrated solutions of $I_5^-$ and $I_3^-$ ions. The resin, which is reacted in chloride form, is contacted with a heated aqueous solution containing high total molalities of $I_5^-$ and $I_3^-$ ions. The contacting is preferably carried out by incremental addition of the resin to the total volume of the solution for converting a predetermined amount of resin. $I_5^-$ and $I_3^-$ ions exchange directly for the $Cl^-$ ions. The released chloride ions are washed out of the resin to leave a stable resin product of predetermined $I_5^-$ content, the remaining exchanged sites being $I_5^-$ sites. The mole ratio of $I_5^-$ to $I_3^-$ can vary from 40% $I_5^-$ with 60% $I_3^-$ to 100% $I_5^-$ with 0% $I_3^-$. In preferred embodiments, the mole ratio of $I_5^-$ to $I_3^-$ is from 50 to 90% $I_5^-$ to 50 to 10% $I_3^-$. Especially effective disinfectant resins are prepared when the treating solution contains from 60 to 80% $I_5^-$ to 40 to 20% $I_3^-$.

The treating solution is prepared by dissolving alkali metal iodide salt in a limited volume of water. For example, from 8 to 10 gram moles of potassium iodide can be dissolved per liter of water to produce 8 to 10 molal solutions of $I^-$. Preparing such high concentrations requires heating of the solution, especially since the dissolving of the solid alkali metal iodide is endothermic. Typical temperatures are in the range from 40° to 50° C.

After the iodide solution has been prepared at the required elevated temperature and molality, granular (solid) iodine ($I_2$) is added. As the $I_2$ dissolves, it forms the $I_3^-$ and $I_5^-$ ions by reacting with the $I^-$ ion. This reaction is endothermic, so heat must be added to maintain the temperature. The amount of iodine added is carefully controlled according to a predetermined calculation so that substantially all of the $I^-$ is converted to either the $I_3^-$ or $I_5^-$ forms without leaving either undissolved iodine or unreacted iodine in solution.

For the contacting, the resin granules can be in a moist, swollen condition, but they preferably are substantially free of external water, which can dilute the treating solution. The contacting is carried out on a batch basis with incremental addition of the resin granules. Typically, the contacting proceeds to completion so that the resin contains exchanged $I_5^-$ and $I_3^-$ in the same proportions as the treating solution.

The process of this invention has many advantages. No special equipment is required, the contacting being carried out in an ordinary covered vessel equipped for gentle stirring. The process can be scaled up, since the size of the batch of resin to be treated is limited only by the physical size of the equipment, and the ability of the operator to manipulate it. It is desirable to carry out the contacting in a closed vessel, since at the elevated temperatures used there is a tendency for some of the iodine to be vaporized from the solution. Regardless of the size of the batch being treated, the entire reaction and conversion of the resin can be completed in a few hours.

In preferred embodiments, substantially all of the exchange sites of the resin are $I_5^-$ or $I_3^-$ and the $I_5^-$ sites predominate, for example, as indicated above, from 60 to 80% of the sites may be $I_5^-$ and 40 to 20% $I_3^-$. This assures the resin will be highly effective as a disinfectant for bacteria, virus and Giardia. The demand release of the disinfecting iodine species will be primarily from the $I_5^-$ sites, since the extra $I_2$ on these sites is more readily released than the $I_2$ associated with the $I_3^-$ sites. Also, the stability of the resin is protected by the $I_3^-$ sites since $I_2$ released from the $I_5^-$ sites can recombine with the $I_3^-$ site to reform $I_5^-$ sites.

DETAILED DESCRIPTION

The method of this invention can be practiced with any strong base anion exchange resin. Such resins are commercially available in the form of granules or "beads" prepared for ion exchange use, and are typically provided in the chloride or sulfate form. For the purpose of this invention the resin is preferably obtained in the chloride form. If necessary, however, it can be converted to the chloride form by ion exchange.

Commercially available quaternary ammonium anion exchange resins which can be used in practicing the present invention include Rexyn 201 (Fisher Scientific Co.), Amberlite IRA-400 and Amberlite IRA-401 SI Rohm & Haas Company), Ionac ASB-1 (Ionac Company), Dowex I and Dowex 21K (Dow Chemical Co.), and Duolite A-101D and A-109 (Diamond Shamrock Chemical Co.). These resins all have quaternary ammonium ion exchange groups, and are supplied in the salt form, usually as the chloride or sulfate, and are in the form of porous granules or "beads" of various mesh sizes.

Other strong base anion exchange resins can be employed, such as tertiary sulfonium resins, quaternary phosphonium resins, and alkyl pyridinium resins. (See (U.S. Pat. No. 3,817,860, col. 3, lines 12-29; and Fina and Lambert 1975), pages 53-54.)

For purpose of the present invention, it is preferred that the resin contain substantially all of the exchange sites in the form of quaternary groups. The resins identified above are supplied in that form. However, if required, the resin can be treated with a methylating agent. This procedure has been referred to as "resin remethylation". It is described in U.S. Pat. No. 4,238,477 and Hatch, et al. (1980), cited above.

The preferred strong base quaternary ammonium anion exchange resins are styrene resins having polystyrene backbone with the anion exchange sites connected to the backbone through phenylmethyl chains. As described in Hatch, et al. (1980), cited above, the presence of a phenyl group contiguous to the basic nitrogen group assists in stabilizing the resin after conversion to the polyiodide form.

In the key step of the process of this invention, granules of the quaternary anion exchange resin in chloride ($Cl^-$) form are contacted with an aqueous solution containing a highly concentrated mixture of $I_3^-$ and $I_5^-$ ions. An elevated temperature is used such as a temperature at least within the range from 30° to 60° C. The combined concentration of the $I_3^-$ and $I_5^-$ ions should be at least equal to 8 molal. Preferably, at least 70% of the anion exchange sites of the resin are exchanged from $Cl^-$ for $I_5^-$ or $I_3^-$. The required amount of $I_5^-$ and $I_3^-$ ions in the contacting solution are calculated so as to be stoichiometrically sufficient to obtain the desired conversion. After the reaction is completed, the resin granules and residual liquid will contain a high concentration of chloride ($Cl^-$) ions. The chloride can be removed by washing the granules with water. Stable polyiodide resins are thereby produced with predetermined proportions of $I_5^-$ and $I_3^-$. Predetermined proportions of $I_5^-$ and $I_3^-$ sites on completion of the reaction are illustrated in Tables I and II.

TABLE I

| Products | Equivalent Ratios | | | % total Sites Iodinated |
|---|---|---|---|---|
| | Resin | $I_2$ | $I^-$ | |
| A | 1.0 | 1.65 | .97 | 97 |
| B | 1.0 | 1.55 | .97 | 97 |
| C | 1.0 | 1.46 | .97 | 97 |
| D | 1.0 | 1.58 | .90 | 90 |
| E | 1.0 | 1.40 | .80 | 80 |

TABLE I-continued

| Products | Equivalent Ratios | | | % total Sites Iodinated |
|---|---|---|---|---|
| | Resin | $I_2$ | $I^-$ | |
| F | 1.0 | 1.22 | .70 | 70 |

TABLE II

| Products | % Iodinated Sites $I_5^-$ | % Iodinated Sites $I_3^-$ | % Total Sites $I_5^-$ | % Total Sites $I_3^-$ |
|---|---|---|---|---|
| A | 70.0 | 30.0 | 67.9 | 29.1 |
| B | 60.0 | 40.0 | 58.2 | 38.8 |
| C | 50.0 | 50.0 | 48.5 | 48.5 |
| D | 75.0 | 25.0 | 67.5 | 22.5 |
| E | 75.0 | 25.0 | 60.0 | 20.0 |
| F | 75.0 | 25.0 | 52.2 | 17.8 |

As illustrated by Tables I and II, the polyiodide resins may contain on a mole ratio basis from 50 to 75% of $I_5^-$ and from 25 to 50% $I_3^-$. In preferred ratios, the $I_5^-$ is present in a substantially higher proportion than the $I_3^-$. On a mole ratio basis, the resin preferably contains from 65 to 75% $I_5^-$ sites and from 25 to 35% $I_3^-$ sites. In an optimized formulation (Product A of Tables I and II), about 70% of the sites are $I_5^-$ and about 30% are $I_3^-$. To achieve these ratios in the resin, the treating solution will contain a minimum of 1.5 moles of $I_2$ per mole of $I^-$ to 2 moles of $I_2$ per mole of $I^-$, corresponding respectively to 50% $I_5^-$ and 75% $I_5^-$. For 65% $I_5^-$, the treating solution will contain 1.65 moles of $I_2$ per mole of $I^-$.

The amount of conversion of the chloride sites of the resin is from 70 to 99%. For example as illustrated by Table A, conversions up to 97% were obtained. Conversions of 90 to 99% are preferred, while conversions of 96 to 98% are believed to be optimum.

Preferred contacting temperatures for the reactions are from 40° to 50° C., such as approximately 45° C. Preferred solution concentrations are from 8 to 10 molal based on the total combined content of the $I_3^-$ and $I_5^-$ ions. The optimized concentration on the same basis is about 9 molal.

The treating solution is prepared by dissolving alkali metal iodide salt in ion-free water. Potassium iodide is the preferred salt, but sodium iodide can be used or other alkali metal iodide. The water is heated to the temperature to be used for the dissolving and is maintained at that temperature by adding additional heat as required during the dissolving which proceeds endothermically. The temperatures used may be the same as those to be employed for the contacting. Preferred temperatures are from 40° to 50° C., such as approximately 45° C.

After the iodide solution has been formed, such as a potassium iodide solution as preferred, solid granular iodine is added with stirring of the solution. As the iodine dissolves, it forms the $I_3^-$ and $I_5^-$ ions, the initial dissolving forming primarily $I_3^-$ ions and $I_5^-$ ions being primarily formed after most of the $I^-$ has been converted to the $I_3^-$ form. It is desirable to avoid fully saturated conditions, that is, $I^-$ saturation or saturation with $I_3^-$ or $I_5^-$. The objective is to dissolve all of the iodine required for the conversion, leaving no undissolved iodine. For this purpose a combination of temperature and molality is used which assures complete dissolving. For example, one optimized combination is a molality of about 9 based on the total $I^-$ content of the solution, whether in the form of $I^-$, $I_3^-$, or $I_5^-$, and a temperature of 45° C.

The dissolving is preferably carried out in closed system, since some iodine may be evolved as a vapor. At temperatures of about 45° C., the amount of iodine lost through vaporization will increase. It is desired to employ temperatures which minimize such iodine loss while producing the high molality solutions required for the process.

After the treating solution has been produced as described and the amount of resin to be converted has been determined from the exchange equivalent of the resin, the contacting reaction can proceed. The entire volume of the solution to be used for treating the quantity of resin can be placed in a reaction vessel. If all of the resin is added to the container at one time, even though the resin is stirred in the solution, some encrustation of iodine on the outer surfaces of the granules can occur. Also, reaction of the entire resin mass in the solution at one time can result in a less uniform product. It is therefore preferred to use incremental addition of portions of the resin batch. As each increment is added it is stirred until the resin is fully covered by the solution. The objective is to disperse the beads in the treating solution, and redissolve any iodine that may possibly have precipitated. The stirring of the granules should be carried out without rupturing or fragmenting the granules. Gentle stirring is therefore advisable.

The amount of treating solution should be sufficient to completely cover the granules after the entire batch of granules has been added. Stated otherwise, the granules should be completely immersed in the solution throughout the conversion process. As the conversion progresses, granules become more dense by shrinking in size. The final size of the body of granules in the solution will therefore be of smaller volume than the original volume of the granules before treatment.

After the resin has been completely reacted, the depleted solution is removed, for example, by drainage through a sieve retaining the granules. Then the granules are washed with water to completely remove exchanged chloride ($Cl^-$) and unreacted material. The resin may be washed on a batch basis or washed in a column. The washing does not remove the triiodide or pentaiodide, which are stabilize on the basic nitrogen sites. The water used for the washing is preferably ion-free.

The method of this invention in an optimized embodiment is illustrated by the following example.

EXAMPLE

To prepare Product A of Table I (with 70% of the iodinated sites $I_5^-$ sites and with 97% of the total sites iodinated), the following stepwise procedure can be used.

1. Measure appropriate wet volume of Chloride ($Cl^-$) form of resin.
    (a) To determine the volume needed, see Calculation Procedures, step 1, as a guide.
    (b) Use the $Cl^-$ form of a Type 1, approximately 8% divinylbenzene crosslinked, polystyrene, quaternary ammonium, strongly basic, an-on exchange resin.
    (c) Be sure resin has had sufficient time to "soak".
    (d) Allow res n to settle in measuring container. Tapping and shaking of container may be needed to insure settling.

(e) Add sufficient water to cover resin. Heat and maintain at 45° C. until used in step 6.

2. Measure appropriate amount of potassium iodide (KI) and place in reaction container.
   (a) To determine the weight needed, see Calculation Procedures, step 2, as a guide.

3. Add measured amount of heated distilled water to reaction container to dissolve KI.
   (a) To determine the volume needed to produce a 9.0 molal solution, see Calculation Procedures, step 3, as a guide.
   (b) The initial water temperature should be high enough that the temperature of the solution in the reaction container can be easily maintained at 45° C. If necessary, heat may be added.
   (c) The KI will not completely dissolve at this concentration unless the 45° C. temperature is maintained.

4. To the 45° C. KI solution, add the measured amount of iodine ($I_2$) needed for the desired triiodide ($I_3$)—pentaiodide ($I_5$) formulation.
   (a) To determine the weight needed, see Calculation Procedures, step 4, as a guide.
   (b) Measure the $I_2$ and then immediately add it to the KI solution. The $I_2$ cannot be measured ahead of time due to its volatility.
   (c) Use all appropriate precautions for handling volatile chemicals.
   (d) Be sure the $I_2$ does not adhere to the sides of the reaction container above the KI solution. Undissolved $I_2$ interferes with proper formation of the resin-$I_5$.

5. Prepare the triiodide-pentaiodide ($I_3$-$I_5$) solution by dissolving the $I_2$ in the KI solution with gentle agitation and heating of the reaction container (to maintain the 45° C.).
   (a) Container should be sealed until the iodine is completely dissolved.
   (b) Heating will be necessary to maintain the temperature at 45° C., since the reaction is endothermic.
   (c) Agitate solution in a fashion that prevents splashing onto the sides of the container.
   (d) The iodine must be completely dissolved. Continue agitation and heating (limit 45° C.) until there are no undissolved particles remaining.

6. Prepare the measured $Cl^-$ form of resin (step 1) for addition to $I_3^-$ and $I_5^-$ solution.
   (a) Remove excess water above and surrounding the beads. Do this by either a drain in the bottom of the container or by inserting a tube to the bottom of the resin and removing the water by suction or siphon. In either case, use care not to remove any resin.
   (b) Proceed to step 7 without delay so that beads will remain moist and at 45° C.

7. Add the prepared and measured $Cl^-$ form of resin (step 6) to the $I_3^-$-$I_5^-$ solution.
   (a) Add the resin in increments to the solution. A scoop or similar device may be used. Be sure none of the resin adheres to the mouth or sides of the reaction container.
   (b) After each increment of resin is added, agitate the reaction container as before. This will disperse the beads, cover them with solution, and redissolve any $I_2$ that may have precipitated due to water added in the resin increment.
   (c) Do not add water along with the resin. If any water appears in the resin container, remove it as outlined in step 6a above, before continuing.

8. Allow the resulting polyiodide resin to stand at room temperature until adsorption is complete.
   (a) Observe the color of the supernatant. When the color no longer changes, the reaction is complete.
   (b) Occasional swirling of the polyiodide resin will speed up the adsorption.

9. Wash the polyiodide resin.
   (a) Remove (as in step 6a) and discard all the liquid above and surrounding the polyiodide resin.
   (b) Add a volume of distilled water equal to approximately double the volume of the polyiodide resin. Let stand for at least 15 minutes, swirling occasionally
   (c) Repeat steps 9a and 9b testing each discarded wash for iodine residual, until the desired concentration is reached.

CALCULATION PROCEDURES

The information needed for the calculations is listed below (values used for the sample calculations are given in parentheses).

| | | |
|---|---|---|
| A. | Final volume of resin-$I_5$ desired | (10 liters) |
| B. | Exchange capacity of resin, wet volume | (1.4 eq/l) |
| C. | Desired % resin sites triiodinated | (97%) |
| D. | Desired % $I_3^-$ sites pentaiodinated | (70%) |
| E. | Equivalent weight of Potassium Iodide | (166.01 g/eq) |
| F. | Equivalent weight of Iodine | (253.80 g/eq) |
| G. | Volume $Cl^1$ form of resin needed | (see Step 1) |
| H. | Weight potassium iodide needed | (see Step 2) |
| Note: | | |
| 1. | Values for Items A, C and D may be changed as desired to fit requirements. | |
| 2. | Value for B varies for each resin and is supplied by the manufacturer. | |
| 3. | E and F are constants. | |
| 4. | Values for G and H will be calculated during Steps 1 and 2 below. | |

Sample Calculation

| | |
|---|---|
| Step 1. | Volume $Cl^-$ form of resin needed (compensate for 12.2% shrinkage) |
| Formula: | (A) ÷ (.878) = liters resin needed |
| Example: | (10 liters) ÷ (.878) = 11.390 liters $Cl^-$ form of resin |
| Step 2. | Weight potassium iodide needed. |
| Formula: | (G · B · E · C) = grams potassium iodide needed |
| Example: | (11.390 l) (1.4 eq/l) (166.01 g/eq) (.97) = 2568 g KI |
| Step 3. | Volume water needed |
| Formula: | (H ÷ E) ÷ (9 mole/kg) = kilograms water needed |
| Example: | (2568 g ÷ 166.01 g/mole ÷ (9 mole/kg) = 1.719 kg water |
| | 1.719 kg water equal 1.719 liters |
| Step 4. | Weight iodine needed |
| Formula: | (G · B · F · C) + (G · B · F · C · D) = grams iodine needed |
| Example: | (11.390 l) (1.4 eq/l) (253.809 g/eq) (.97) = 3926 g $I_2$ |
| | (11.390 l) (1.4 eq/q) (253.809 g/eq) (.97) (.70) = 2748 g $I_2$ |
| | Total 6674 g $I_2$ |

We claim:

1. The method of directly preparing a polyiodide quaternary ammonium anion exchange resin disinfectant capable of killing Giardia, said resin disinfectant containing $I_5^-$ exchange sites and $I_3^-$ exchange sites and said resin disinfectant being prepared from an aqueous solution of an iodide ($I^-$) salt and elemental iodine ($I_2$), comprising:
   (a) preparing salt aqueous solution by dissolving the iodide salt therein to an $I^-$ concentration of 8 to 10 molal at a temperature in the range from 30° to 60° C;

(b) adding iodine ($I_2$) to said solution to obtain a combined concentration of $I_5^-$ and $I_3^-$ ions of about 8 to 10 molal, at least 50% of said ions being $I_5^-$ ions;

(c) contacting granules of a strong base anion exchange resin in the chloride ($Cl^-$) form with the solution formed in steps (a) and (b) at a temperature in the range from 30° to 60° C., said resin being reactable with $I_5^-$ and $I_3^-$ ions;

(d) continuing said contacting until at least a total of 70% of the anion exchange sites of the resin have exchanged $Cl^-$ for $I_5^-$ and $I_3^-$, the exchange being in the $I_5^-$ and $I_3^-$ proportions of said solution and continuing the exchange until 50 percent of the exchange sites are $I_5-$ exchange sites; and (e) washing said resin with an aqueous wash to remove the exchanged $Cl^-$ ions therefrom.

2. The method improvement of claim 1 in which said anion exchange resin is a quaternary ammonium anion exchange resin.

3. The method improvement of claim 2 in which the solution is formed in steps (a) and (b) at a temperature of from about 40° to 50° C., and the resin is contacted with said solution in steps (c) and (d) at a temperature of from about 40° to 50° C.

4. The method improvement of claims 1 or 2 in which the aqueous solution formed in steps (a) and (b) contains a stoichiometric amount of $I_5^-$ and $I_3^-$ in relation to the amount of said resin granules to be contacted in steps (c) and (d) to exchange from about 90 to 99% of its chloride sites, and step (d) is continued until from about 90 to 99% of said chloride sites are exchanged in the $I_5^-$ and $I_3^-$ proportions of said solution.

5. The method improvement of claims 1 or 2 in which the aqueous solution formed in steps (a) and (b) has a combined concentration of $I_5^-$ and $I_3^-$ ions of from about 8.5 to 9.5 molal and said solution is essentially free of undissolved iodine when it is contacted with the resin granules in steps (c) and (d).

6. The method of directly preparing a polyiodide quaternary ammonium anion exchange resin disinfectant capable of killing Giardia, said resin disinfectant containing $I_5^-$ exchanges sites and $I_3^-$ exchange sites and said resin disinfectant being prepared from a aqueous solution of an iodide ($I^-$) salt and elemental iodine ($I_2$), comprising:

(a) preparing said aqueous solution by dissolving the iodide salt therein to an $I^-$ concentration of 8 to 10 molal at a temperature in the range from 40° to 50° C.;

(b) adding iodine ($I_2$) to said solution to obtain a combined concentration of $I_5^-$ and $I_3^-$ ions of about 8 to 10 molal, from 50 to 90% of said ions being $I_5^-$ ions;

(c) contacting granules of a strong base quaternary ammonium anion exchange resin in the chloride ($Cl^-$) form with the treating solution formed in steps (a) and (b) at a temperature within the range from 40° to 50° C., said resin being reactable with $I_5^-$ and $I_3^-$ ions;

(d) continuing said contacting until at least a total of 70% of the anion exchange sites of the resin have exchanged $Cl^-$ for said $I_5^-$ and $I_3^-$, the exchange being in the $I_5^-$ and $I_3^-$ proportions of the said solution and continuing the exchange until 50 percent of the exchange sites are $I_5-$ exchange sites; and (e) washing said resin with an aqueous wash to remove the exchanged $Cl^-$ ions therefrom.

7. The method improvement of claim 6 in which the solution formed in steps (a) and (b) contains from 60 to 80% $I_5^-$ and 20 to 40% $I_3^-$.

8. The method improvement of claims 6 or 7 in which the aqueous solution formed in steps (a) and (b) contains a stoichiometric amount of $I_5^-$ and $I_3^-$ in relation to the amount of said resin granules to be contacted to exchange from about 90 to 99% of its chloride sites, and step (d) is continued until from about 90 to 99% of said chloride sites are exchanged in the $I_5^-$ and $I_3^-$ proportions of said solution.

9. The method of claims 1 or 6 in which said granules are formed of a styrene resin having quaternary ammonium sites linked to the styrene backbone by polymethyl chains.

* * * * *